United States Patent [19]

Bunge et al.

[11] Patent Number: 4,725,621

[45] Date of Patent: Feb. 16, 1988

[54] CL-1957E ANTIBIOTIC COMPOUND AND ITS PRODUCTION

[75] Inventors: Richard H. Bunge; James C. French; Timothy R. Hurley; Neil E. Willmer, all of Ann Arbor, Mich.

[73] Assignee: Warner-Lambert Company, Morris Plains, N.J.

[21] Appl. No.: 835,825

[22] Filed: Mar. 3, 1986

[51] Int. Cl.$^4$ ............... A61K 31/365; C07D 309/30
[52] U.S. Cl. ........................... 514/460; 549/294
[58] Field of Search ............... 424/122; 549/420, 294; 514/460

[56] References Cited

U.S. PATENT DOCUMENTS 4,148,882 4/1979 Celmer et al. .............. 424/122

Primary Examiner—Nicky Chan
Attorney, Agent, or Firm—Jerry F. Janssen

[57] ABSTRACT

A purified isolate of an actinomycete identified as ATCC 39366 is capable of producing the antimicrobial compound CL-1957E which also exhibits antitumor properties.

The antimicrobial compound CL-1957E is produced by cultivating isolate ATCC 39366 under aerobic conditions in a culture medium containing assimilable sources of carbon and nitrogen until a substantially quantity of the CL-1957E compound is produced, and subsequently isolating the CL-1957E compound.

The antibiotic compound CL-1957E and pharmaceutical compositions comprising this substance together with a pharmaceutically acceptable carrier is also disclosed, as are methods of treating microbial infections and tumors in mammals, employing these pharmaceutical compositions.

10 Claims, 4 Drawing Figures

CL-1957E ANTIBIOTIC COMPOUND AND ITS PRODUCTION

BACKGROUND OF THE INVENTION

The present invention relates to an antibiotic compound demonstrating antitumor activity, designated CL-1957E, to pharmaceutically acceptable salts thereof, to a process for the production of said compound, and to a purified isolate of an actinomycete capable of producing this compound.

More particularly, the process of producing the CL-1957E antibiotic compound relates to an aerobic fermentation process using a purified isolate of an actinomycete, identified as isolate ATCC 39366.

SUMMARY OF THE INVENTION

In accordance with one aspect of the present invention, there is provided a process for producing CL-1957E by cultivating the isolate of actinomycete identified as ATCC 39366 under aerobic conditions in a medium containing assimilable sources of carbon and nitrogen until a substantial quantity of CL-1957E is produced, and subsequently isolating the CL-1957E compound.

In accordance with another aspect of the invention, there is provided the antibiotic compound CL-1957E or a pharmaceutically acceptable salt thereof.

In another aspect of the present invention, there are provided pharmaceutical compositions comprising the CL-1957E compound, or a pharmaceutically acceptable salt and, optionally, additional antibiotic and/or antitumor compounds together with a pharmaceutically acceptable carrier.

In a further aspect of the present invention, a method of treating microbial infections in a mammal comprises administering an effective amount of the compound CL-1957E or a pharmaceutically acceptable salt thereof in combination with a pharmaceutically acceptable carrier.

In another aspect of the present invention, a method of treating tumors in mammals comprises administering an effective amount of the compound CL-1957E or a pharmaceutically acceptable salt thereof in combination with a pharmaceutically acceptable carrier.

DETAILED DESCRIPTION

Figure 1:
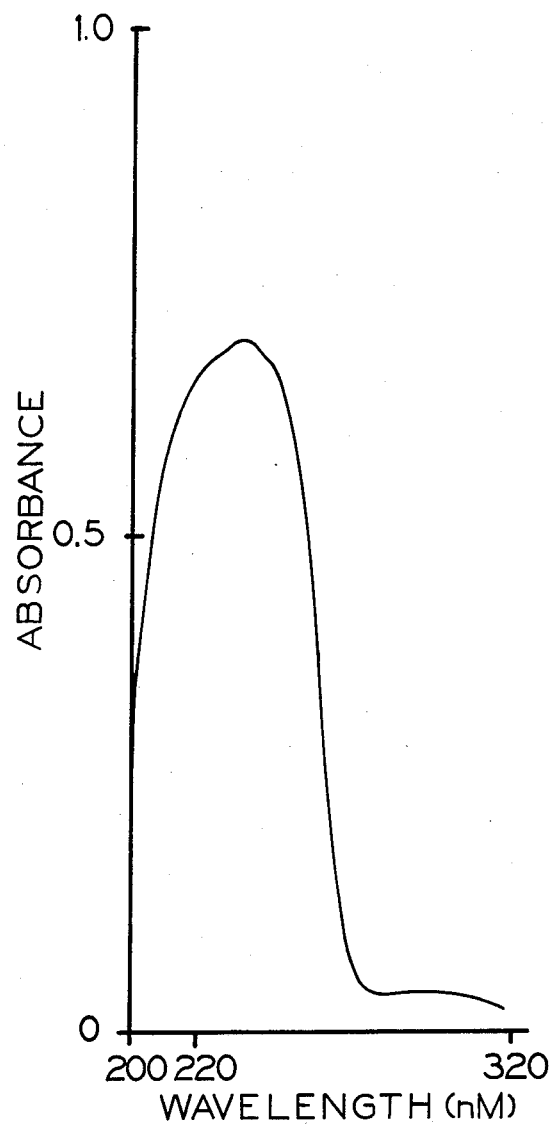
FIGS. 1, 2, 3, and 4 are the ultraviolet, infrared, 200 MHz proton magnetic resonance, and 75.4 MHz $^{13}$C nuclear magnetic resonance spectra, respctively, of the compound designated CL-1957E.

In accordance with the present invention, the CL-1957E antibiotic compound is produced by cultivating a purified isolate of actinomycte, isolate ATCC 39366, under aerobic conditions until a substantial quantity of CL-1957E is formed, and subsquently isolating the compound.

The strain of actinomycete suitable for the purpose of this invention was found in a soil sample collected in Pennsylvania, USA. This microorganism was isolated from the soil sample using a suitable agar plating medium, one containing salts such as potassium phosphate, magnesium sulfate, and ferrous sulfate, and carbon sources such as glycerol and asparagine. The strain of microorganism was plated onto the agar medium and, once plated, was incubated at a favorable temperature, particularly 45° C., to allow for the development of the soil microorganisms.

The CL-1957E producing organism that was isolated from the soil sample by the agar plating technique is an unidentified isolate of actinomycete and has been deposited with the American Type Culture Collection, Rockville, Md. 20852, where it is being maintained in their permanent culture collection as ATCC 39366. This organism, which produces CL-1957E, is also being maintained as a dormant culture in lyophile tubes, cryogenic vials, and in soil tubes in the Warner-Lambert/Parke-Davis Culture Collection, 2800 Plymouth Road, Ann Arbor, Mich. 48105, where it is designated as culture WP-2053. spores were produced in a spiral chain with 10 or more spores in a chain. The spores were smooth and cylindrical or rectangular in shape.

TABLE 1

| Medium* | Color** |
|---|---|
| Yeast extract - malt extract agar (ISP-2) | Slate gray (aerial mycelia) Mustard gold (reverse substratal mycelium) |
| Oatmeal agar (ISP-3) | No color (aerial mycelia) Olive (reverse substratal mycelium) |
| Inorganic salts - starch agar (ISP-4) | Pewter gray (aerial mycelia) No color (reverse substratal mycelium) |
| Glycerol - asparagine | Near gray (aerial mycelia) Light wheat (reverse substratal mycelium) |

*Media compositions given in Shirling, et al., Int. J. Syst. Bacteriol., 16: 313-340 (1966).
**Color designation from Color Harmony Manual, 4th Ed., Container Corporation of America, 1958.

The cell wall of isolate ACTCC 39366 contained L,L-diaminopimelic acid and glycine which are characteristic of type I cell wall. A unique feature of the organism was the presence of a major amount of arabinose which was found upon whole cell analysis.

The isolate was found to reduce nitrate, liquefy gelatin, and peptonize milk. Melanin or other soluble pigments were not formed. As shown by the data appearing in Table 2, the culture utilized ten of the sixteen carbon sources tested; it did not utilize arabinose, inulin, lactose, maltose, mannitol or sucrose.

TABLE 2

| Carbon Source | Utilization* |
|---|---|
| L-Arabinose | − |
| D-Fructose | + |
| D-Galactose | + |
| D-Glucose | + |
| Glycerol | + |
| i-Inositol | + |
| Inulin | − |
| Lactose | − |
| Maltose | − |
| D-Mannitol | − |
| D-Mannose | + |
| Raffinose | + |
| Rhamnose | + |
| Salicin | + |
| Sucrose | − |
| D-Xylose | + |
| Control (no carbon source) | − |

*"−" = No growth; "+" = Good growth.

The compound CL-1957E, which demonstrates both antibiotic and antitumor properties, is produced by isolate ATCC 39366 during aerobic fermentation under controlled conditions. The fermentation medium consists of sources of carbon, nitrogen, minerals, and growth factors. Examples of carbon sources are glycerol and various simple sugars, such as glucose, mannose, fructose, xylose, ribose, or other carbohydrate-containing compounds such as dextrin, starch, cornmeal, and whey. The normal quantity of carbon source materials in the fermentation medium varies from about 0.1 to about 10 weight percent.

Nitrogen sources in the fermentation medium are organic, inorganic, or mixed organic-inorganic material. Examples of such materials are cottonseed meal, soybean meal, corn germ flour, corn steep liquor, distillers dried solubles, peanut meal, peptonized milk, and various ammonium salts.

The addition of minerals and growth factors are also helpful in the production of the CL-1957E compound. Examples of fermentation medium mineral additives include potassium chloride, sodium chloride, ferrous sulfate, calcium carbonate, cobalt chloride, and zinc sulfate. Sources of growth factors include various yeast and milk products.

The preferred method for producing the CL-1957E compound is by submerged culture fermentation. According to this embodiment of the invention, the fermentation ingredients are prepared in solution or suspension and the mixture subsequently sterilized by autoclaving or steam heating. The pH of the aqueous medium is adjusted to preferably between about pH 4 and about pH 8 and the mixture cooled following sterilization to a temperature between about 16° C. to about 45° C. The cooled, sterile fermentation medium is inoculated with the organism and thereafter fermentation is carried out with aeration and agitation.

In the submerged culture medium, fermentation is carried out in shake-flasks or in stationary tank fermentors. In shake-flasks, aeration is achieved by agitation of the flasks to bring about mixing of the medium with air. In stationary tank fermentors, agitation is provided by impellers which may take the form of disc turbines, vaned discs, open turbine or marine propellers. Aeration is accomplished by injecting air or oxygen into the agitated mixture.

Adequate production of the CL-1957E compound is normally achieved under these conditions after a period of about two to ten days.

In an alternative embodiment, the CL-1957E compound may also be produced by solid state fermentation of the microorganism.

The following examples are provided to enable one skilled in the art to practice the present invention and are merely illustrative thereof. They are not to be viewed as limiting the scope of the invention as defined by the appended claims.

Fermentative Production of the CL-1957E Compound

EXAMPLE 1

Stage I See (2-liter flask)

The contents of one lyophile tube containing actinomycete isolate, ATCC 39366, are aseptically inoculated into one baffled 2-liter Erlenmeyer seed flask containing 600 ml of sterilized SD-14 seed medium.

The seed flask is placed on an gyrotory shaker, 130 rpm, and incubated at 24° C. After approximately 72 hours, the flask is visually inspected and checked for asepsis microscopically by wet mount and Gram stain.

TABLE 3

| Formulation of SD-14 Seed Medium | | |
|---|---|---|
| Ingredient | Amount | Supplier |
| Cerelose | 20.0 g | Corn Products |
| Torula Yeast | 2.0 g | Lake States |
| O.M. Peptone | 5.0 g | Universal Foods |
| Nutrisoy Flour | 10.0 g | Archer Daniels |
| NaCl | 1.0 g | Generic |
| $CaCO_3$ | 2.5 g | Generic |
| Deionized Water | 1000.0 ml | |

EXAMPLE 2

Stage II Seed (30-liter stirred-jar)

The contents of one Stage I seed flask is used to aspectically inoculate one stirred-jar for Stage II seed. Two stirred-jar fermentors which are 30-liter stainless steel tanks are used. Each seed stirred-jar contains 15.4 liters of SD-14 seed medium, autoclaved for 90 minutes. The seeded stirred-jars are incubated at 24° C., 300 rpm, and sparged with air at a rate of 16 liters/minute (1 volume/volume/minute). Excess foaming is monitored by a conductance probe and controlled by addition of SWS Q97 silicon antifoam (1:1 silicon oil:water) on demand. Both seed stirred-jars are sampled pre- and postinoculation and processed for pH, sedimentation (a 15 ml sample in a 15-ml conical centrifuge tube, X450G, 12 minutes), sterility (Tryptic Soy Agar plate and Nutrient Broth with pH indicator), carbohydrate (Lilly Tes-Tape glucose enzymatic test strip), and $CO_2$ (IR Detector). After approximately 48 hours, the seed stirred-jars are again sampled and processed as above. About 0.25% glucose should remain and the $CO_2$ should be in the 0.05% range.

EXAMPLE 3

Stage III Seed (757-liter fermentor)

The contents of one stirred-jar is used to aseptically inoculate one 757-liter fermentor for Stage III seed. The fermentor contains 265 liters of SD-14 seed medium, sterilized by jacket and sparger steam for 40 minutes at 121° C. The seeded fermentor is incubated at 24° C., 190 rpm, and a 7.5 cfm (0.75 volume/volume/minute) aeration rate. Excess foaming is monitored by a conductance probe and controlled by addition of SWS Q97 silicone antifoam (1:1 silicon oil:water) on demand. The seed fermentor is sampled both pre- and postinoculation as described in Example 2. After approximately 48 hours the fermentor is again sampled and processed as previously outlined. Approximately 0.25% glucose will remain and the $CO_2$ will be in the 0.06-0.07% range.

EXAMPLE 4

Production Fermentors (757-liter tanks)

Each of two stainless steel, 750-liter tanks is asceptically filled with 587 liters of PM-10A production medium which is prepared in two stages: (1) the maltose and cerelose are mixed in 55 liters of deionized water and the resulting solution is sterilized with steam for 20 minutes and (2) after cooling, this sterilized carbohydrate solution is asceptically transferred to a 757-liter tank containing the calculated volume (approximately 532 liters) of a sterilized solution of the other PM-10A ingredients. About 19 liters of the Stage II seed prepared as described in Example 3 is transferred asceptically to each of two 757-liter tanks filled with 587 liters of sterile PM-10A production medium.

The fermentation conditions are: 24° C. incubation temperature, 155 rpm impeller speed, and air sparging at a rate of 0.5–1.0 volume/volume/minute. Excess foaming is controlled (capacitance probe) by addition of SWS Q97 silicon antifoam solution (1:1 silicone oil:water) on demand. The production run time is 165 hours.

TABLE 4

Formulation of PM-10A Production Medium

| Ingredient | Amount | Supplier |
|---|---|---|
| Maltose | 15.0 g | Eastern Chemical |
| Cerelose | 10.0 g | Corn Products |
| Pharmamedia | 7.5 g | Traders Protein |
| Corn Meal | 4.0 g | Quaker Oats Co. |
| Torula Yeast | 5.0 g | Lake States |
| Deionized water | 1000.0 ml | |
| adjust to pH 6.5 with NaOH | | |

EXAMPLE 5

Production Fermentor (7570-liter tank)

The production fermentor is a 7570-liter stainless steel tank charged with 4635 liters of PM-10A production medium prepared in two stages. The maltose and cerelose are mixed in 550 liters of deionized water and sterilized in situ for 20 minutes in a separate 757-liter fermentor. The remaining medium ingredients are charged into a sufficient volume of deionized water (about 3900 liters) and sterilized for 40 minutes with sparged steam at 121° C. After cooling, the presterilized carbohydrate solution is aseptically transferred to the production fermentor to provide a preinoculaton volume about about 4635 liters including condensate accumulation during sterilization. The resulting medium is cooled to 24° C. and then inoculated with approximately 550 liters of the inoculation prepared in the Stage III seed fermentor from Example 3.

The fermentation conditions are: 24° C. incubation temperature, 125 rpm impeller speed, and air sparging at a rate of 0.75 volume/volume/minute. Excess foaming is controlled (capacitance probe) by addition of SWS Q97 silicone antifoam solution (1:1 silicon oil:water) on demand. The production run time is 168 hours.

Each of the production tanks is sampled pre- and postinoculation and checked for pH, sedimentation (a 15 ml sample is centrifuged in a clinical centrifuge, 450 g for 12 minutes), sterility (Tryptic Soy Agar plate and nutrient broth with pH indicator), carbohydrate (Lilly Tes-Tape glucose enzymatic test strip), and $CO_2$ generation (IR detector). A typical pH and growth profile is shown in FIG. 5.

The crude fermentation beers from two 757-liter fermentors, prepared as described in Example 4, and from one 7570-liter fermentor as described in Example 5 were harvested and the CL-1957E compound isolated as described below.

Chemical Isolation and Purification of the CL-1957E Compound

Fermentation beer (5879 liters) prepared as described in Examples 4 and 5 was adjusted to pH 3.5 with sulfuric acid and mixed for one hour with ethyl acetate (4347 liters). Celite 545 (205 kg) was added and the mixture filtered through a 79-cm plate-and-frame filter press. The filter cake was washed with ethyl acetate (491 liters) and the wash was added to the filtrate. The upper ethyl acetate layer (4082 liters) was separated and concentrated in vacuo to 54 liters. This concentrate was washed with water and then concentrated further to 15 liters. Petroleum ether (bp 30°–60° C.) (75 liters) was added and the resulting mixture was extracted with 30 liters of methanol-water (9:1) followed by a second extraction using 15 liters of methanol-water (9:1). The aqueous methanol extracts were combined (52 liters) and washed with 8 liters of petroleum ether. The remaining aqueous methanol layer was concentrated in vacuo to remove methanol. During this concentration step, dichloromethane was introduced periodically to the evaporator to afford a concentrate dissolved in 8.5 liters of dichloromethane. One fourth of this concentrate (designated Concentrate A) was diluted to 4 liters with dichloromethane and applied to a 15 cm [i.d.]×180 cm column containing 12 kg of silicic acid-Celite 545 (1:1). After the column was washed with 67 liters of dichloromethane, the silicic acid-Celite 545 was eluted with 83 liters of dichloromethane-methanol (98:2) followed by 45 liters of dichloromethane-methanol (96:4). The latter eluate was combined with the corresponding eluates obtained from the chromatography of the remaining three-quarters of Concentrate A over three separate 12 kg batches of silicic acid-Celite 545 (1:1). This solution (124 liters) of combined eluates was concentrated in vacuo to a residual oil which was dissolved in methanol. The resulting solution was filtered and diluted to 2,200 ml. This solution (designated concentrate B) was used for the chromatographic separation and purification of CL-1957E in the following manner.

A 15 cm [i.d.]×180 cm stainless steel column was packed with 17 kg of C-18 silica gel (Sepralyte C-18, 40 μm particle size, Analytichem International, Harbor City, CA). After the C-18 silica gel was equilibrated with 60 liters of 0.05M ammonium acetate buffer (pH 6.5)-methanol (50:50), a one-third portion (733 ml) of concentrate B was added to the top of the column. Chromatography was then carried out using 0.05M ammonium acetate buffer (pH 6.5)-acetonitrile (62:38) as the mobile phase.

After 80 liters of eluate was collected, the next 32 liters of eluate (collected in four fractions) contained nearly all of the CL-1957E present in the charge. This and all subsequent chromatographic steps, use to separate CL-1957E from its congeners were monitored by high performance liquid chromatography using the following conditions:

Column: 5 μm NovaPak TM 0.4 mm[i.d.]×10 cm C-18 silica gel (Waters Associates, Milford, MA).

Mobile Phase: 0.05M ammonium acetate buffer (pH 6.5)-acetonitrile (53:47)

Detection: UV at 254 nm

Flow Rate: 1.0 ml/min

Retention Time:
CL-1957E—3.0 min
CL-1957B~4.1 min

The remaining two-thirds of concentrate B was chromatographed as above in two equal portions (733 ml) over the same column after the C-18 silica gel was each time regenerated with 40 liters of acetonitrile, 30 liters of methanol, and finally with 60 liters of 0.05M ammonium acetate buffer (pH 6.5)-methanol (50:50). The CL-1957E containing fractions from the above three C-18 silica gel columns were combined (86 liters) and diluted to 124 liters with water. The resulting solution was passed through a 10 cm[i.d.]×120 cm stainless steel column packed with 5.5 kg of 40 µm C-18 silica gel which was preequilibrated with 0.05M ammonium acetate buffer (pH 6.5)-methanol (50:50). After the charge was applied, chromatography was effected using 0.05M ammonium acetate buffer (pH 6.6)-acetonitrile (59:41). After 35 liters of eluate was collected, most of the CL-1957E was eluted in the next 16 liters, collected in 2 liter fractions.

Figure 2:
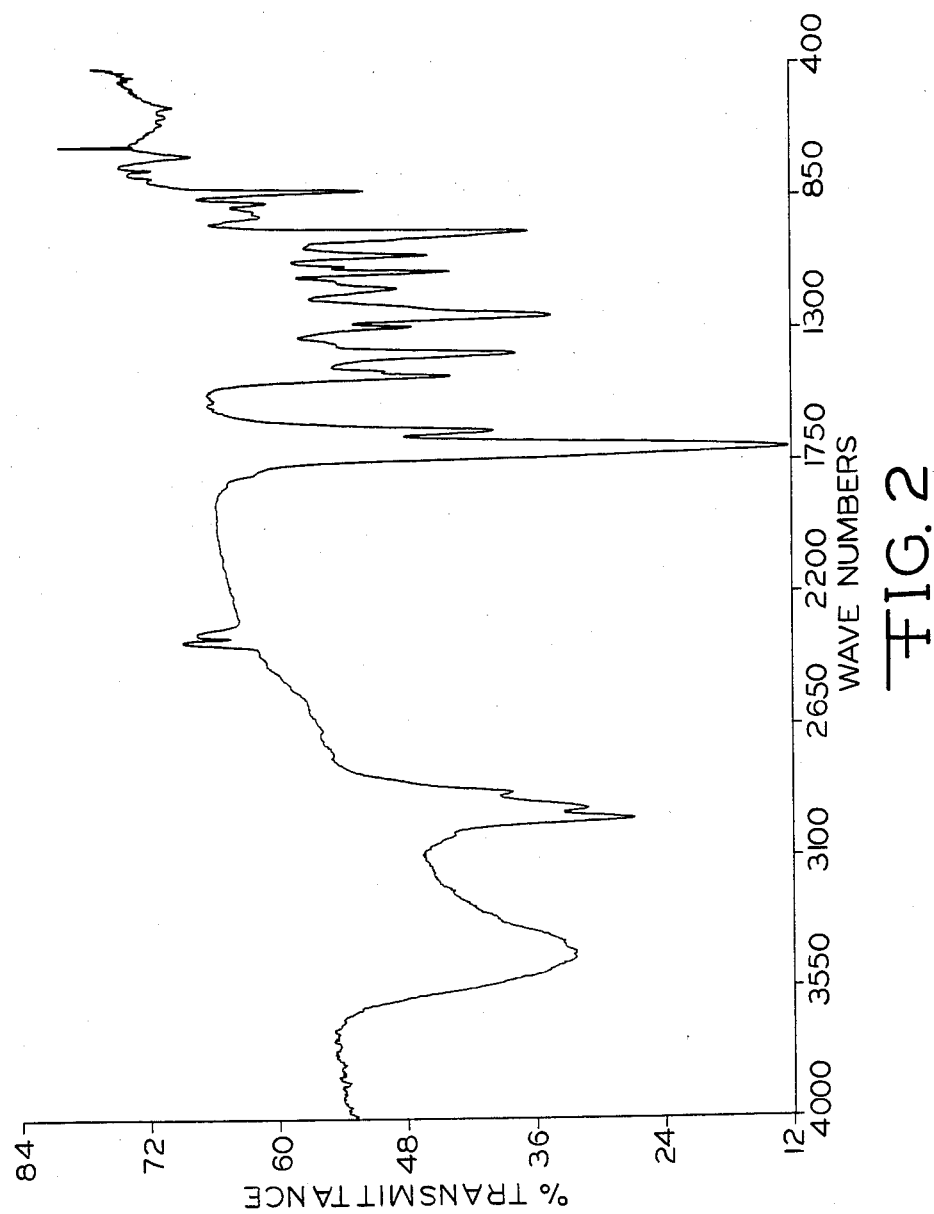
Figure 3:
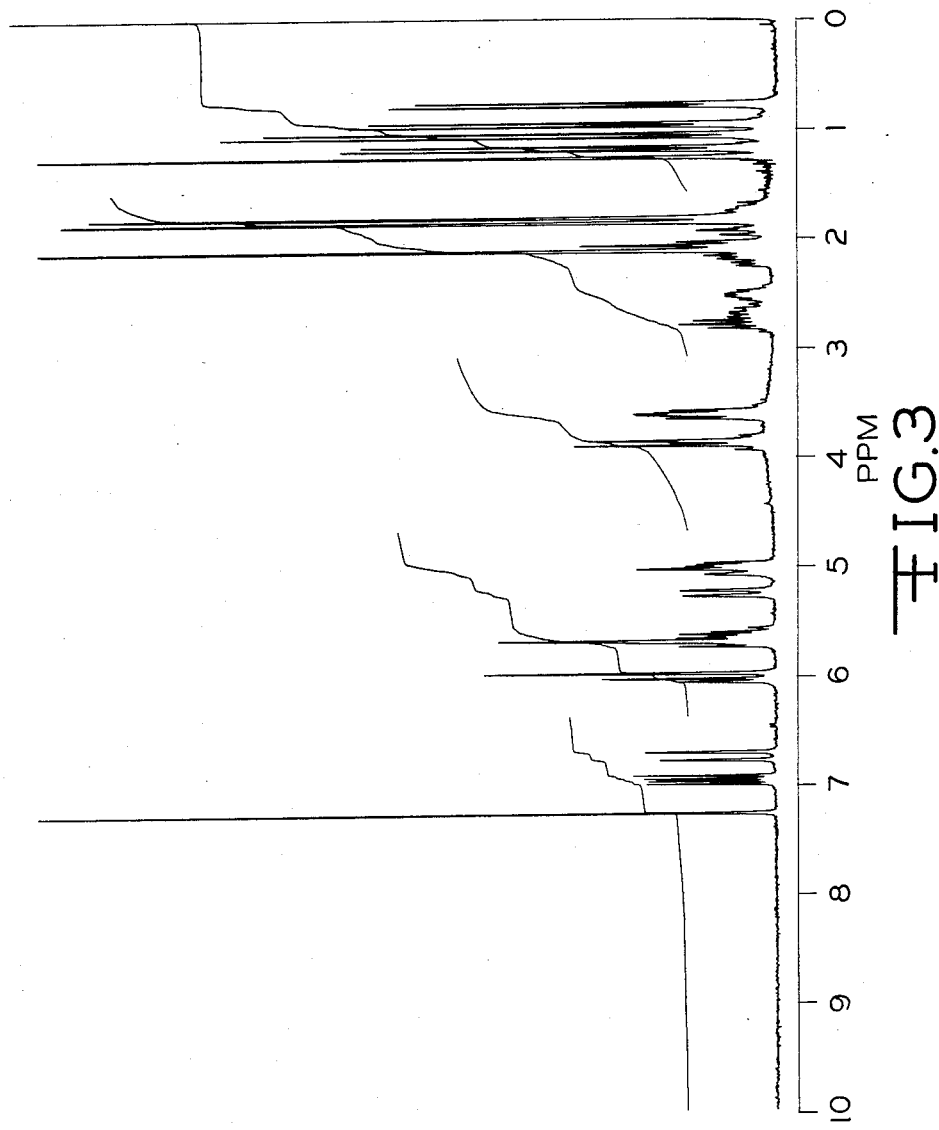
Figure 4:
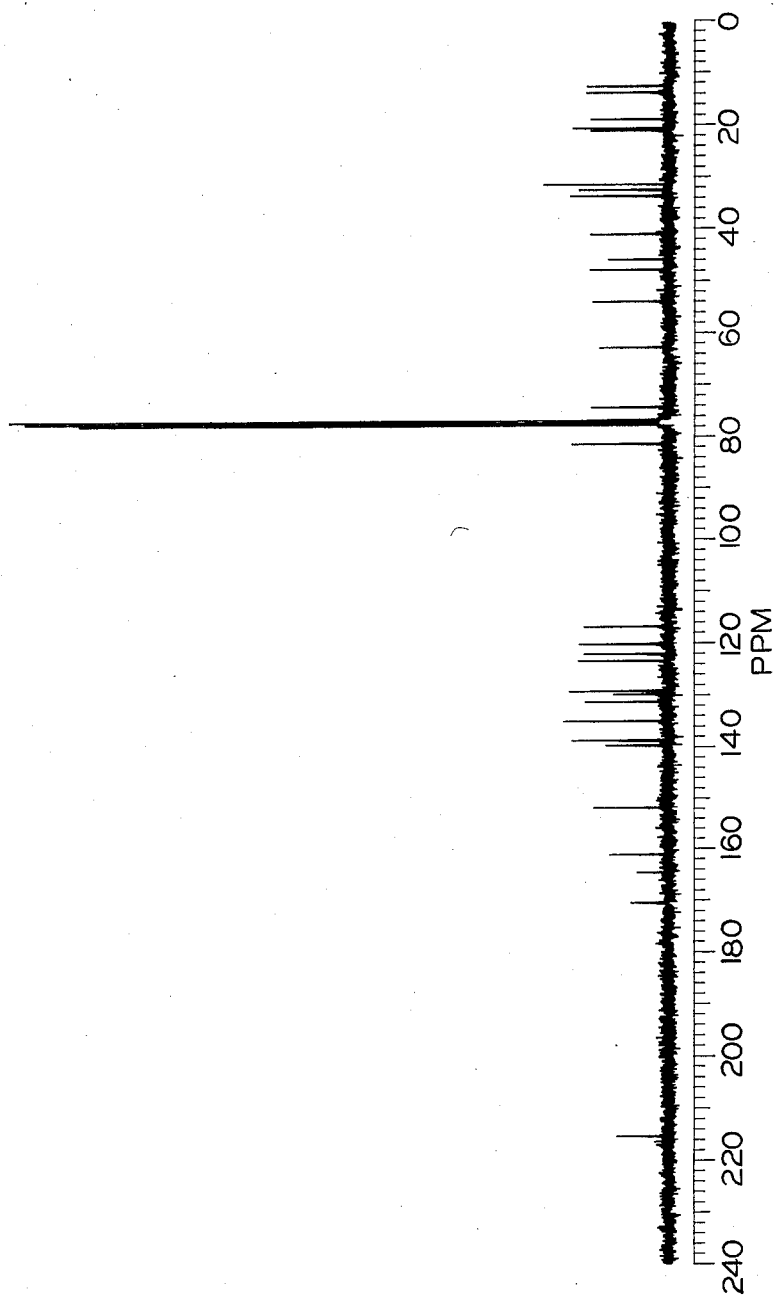

These eight fractions were combined and concentrated in vacuo to 3.2 liters. The evaporator was washed with dichloromethane and this wash was used to extract the 3.2 liters of aqueous concentrate. The layers were separated and the aqueous layer was reextracted two times with dichloromethane. The three dichloromethane extracts were combined and washed two times with one liter portions of water followed by two additional washes using 500 ml portions of water. The remaining dichloromethane layer was dried with anhydrous sodium sulfate, filtered, and evaporated to dryness in vacuo. A diethylether solution of the remaining solid residue was filtered and then evaporated to dryness in vacuo. A solution of the residue in 700 ml of t-butanol was lyophilized to yield 12.48 g of CL-1957E as a pale yellow solid. The chemical and physical properties of CL-1957E appear in Table 5 and the infrared, 200 MHz proton magnetic resonance and 75.4 MHz $^{13}$C nuclear magnetic resonance spectra of CL-1957E appear as FIGS. 1, 2, 3, and 4, respectively.

TABLE 5

| Chemical and Physical Properties of CL-1957E | |
|---|---|
| Property | CL-1957E |
| Molecular weight | 542 atomic mass units |
| Elemental analysis | Calculated for $C_{32}H_{46}O_7 \cdot 0.08$ $H_2O \cdot 0.60$ $C_4H_{10}O$: C, 69.55% H, 8.82%; $H_2O$, 0.81%; $C_4H_{10}O$, 6.15%. Found: C, 69.58%; H, 8.95%; $H_2O$, 1.31%; $C_4H_{10}O$, 6.0% |
| Melting point | 48–50° C. (with prior softening) |
| Optical rotation | $[\alpha]_D^{23}$ -157.6° (0.76% in chloroform) |
| Ultraviolet absorption spectrum (in methanol)[a] | Maxima at 234 nm ($\epsilon$ = 47,100) and 294 nm ($\epsilon$ = 2720) |
| Infrared absorption spectrum (in chloroform) | Principal absorption peaks at 2971, 2935, 1709, 1644, 1457, 1380, 1253, 1160, 1103, 1047, and 968 reciprocal centimeters. |
| 200 MHz proton magnetic resonance spectrum (deuterochloroform solution) | Principal signals at 0.77 (doublet, 3 protons), 0.97 (doublet, 3 protons), 1.07 (doublet, 3 protons), 1.70 (doublet, 3 protons), 1.83 (doublet, 3 protons), 1.85 (doublet, 3 protons), 1.87 (doublet, 3 protons), 2.06 (multiplet, 2 protons), 2.13 (singlet, 3 protons), 2.5–2.9 (multiplets, 3 protons), 3.63 (multiplet, 2 protons), 3.89 (multiplet, 2 protons), 5.0–5.1 (multiplets, 2 protons), 5.26 (doublet, 1 proton), 5.63–5.75 (multiplet, 3 protons) |

TABLE 5-continued

| Chemical and Physical Properties of CL-1957E | |
|---|---|
| Property | CL-1957E |
| | 6.01 (doublet, 1 proton), 6.03 (doublet, 1 proton) 6.75 (doublet 1 proton), and 6.97 (doublet of doublets, 1 proton) parts per million downfield from tetramethylsilane. |
| 75.4 MHz $^{13}$C nuclear magnetic resonance spectrum (deuterochloroform solution) | Principal signals at 215.18 170.30, 164.43, 160.98, 151.67, 139.49, 138.61, 134.88, 131.10, 129.72, 129.02, 123.25, 121.99, 120.06, 116.72, 81.28, 77.23, 74.08, 62.60, 53.74[b], 47.66, 45.58, 40.75, 33.53, 33.41, 32.29, 31.21[b], 20.85, 20.48, 18.60, 13.61, 13.38, 12.36, and 12.21 parts per million downfield from tetramethylsilane |
| Retention time (high pressure chromatography, µBondpak (TM) C-18-silica gel column, 3.9 mm i.d. × 30 cm, Waters Associates, Milford, MA, solvent: 55:45 0.05 M ammonium acetate buffer (pH 6.8)-acetonitrile, flow rate 1.5 ml/min) | 4.1 minutes |
| $R_f$ (thin-layer chromatography on silica gel 60 F254, E. Merck, solvent: toluene-ethyl acetate-methanol-acetic acid (65:27:7:1) | 0.20 |

[a]Molar absorptivity ($\epsilon$) calculated on the basis of included t-butanol and water.
[b]Signal from included t-butanol.

While not holding to particular structures to the exclusion of others, the chemical structure of CL-1957E is believed to correspond to that indicated by Structure I below, which is consistent with the spectral data presented in Table 6 and

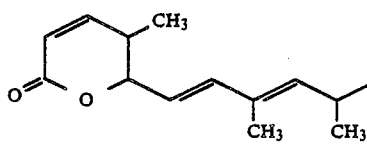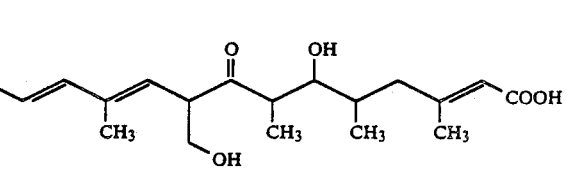

I is 19-(3,6-dihydro-3-methyl-6-oxo-2H-pyran-2-yl)-6-hydroxy-9-(hydroxymethyl)-3,5,7,11,15,17-hexamethyl-8-oxo-2,10,12,16,18-nonadecapentaenoic acid.

Biological Activity of CL-1957E

EXAMPLE 7

The antimicrobial activity of CL-1957E was evaluated using the broth microdilution method. Serial dilutions of CL-1957E were made in Muellar-Hinton broth for bacteria and in yeast extract-peptone-dextrose broth for the fungi. Minimal inhibitory concentrations (MICs) are listed in Table 6.

TABLE 6

| Microorganism | Culture Number | Minimal Inhibitory Concentration (MIC) of CL-1957D (µg/ml) |
|---|---|---|
| Escherichia coli | 04863 | >1000 |
| Salmonella typhimurium | TA1535 | >1000 |
| Alcaligenes viscolactis | 21698 | ≦0.46 |
| Branhamella catarrhalis | 03596 | ≦0.46 |

TABLE 6-continued

| Microorganism | Culture Number | Minimal Inhibitory Concentration (MIC) of CL-1957D (µg/ml) |
|---|---|---|
| Pseudomonas aeruginosa | 05111 | >1000 |
| Micrococcus luteus | 05064 | ≦0.46 |
| Staphylococcus aureus | 02482 | ≦0.46 |
| Streptococcus pyogenes | C203 | ≦0.46 |
| Streptococcus pneumoniae | SV1 | ≦0.46 |
| Streptococcus faecalis | 05045 | ≦0.46 |
| Bacillus cereus | 04810 | ≦0.46 |
| Bacillus megaterium | 066 | ≦0.46 |
| Saccharomyces cerevisiae | S288 | >1000 |
| Schizosaccharomyces pombe | M1388 | 12.3 |
| Rhodotorula aurantiaca | M1508 | >1000 |
| Torulopsis albida | M1390 | >1000 |
| Mucor parasiticus | M2652 | >1000 |
| Rhizopus japonicus | M1557 | >1000 |

EXAMPLE 8

The in vivo activity of CL-1957E against P388 leukemia in mice was assayed using the protocol established in Cancer Chemotherapy Reports, Vol. 3, Part 3, 1–87 (1972). The mice were infected intraperitoneally on Day 0 and then given the dose of CL-1957E indicated in Table 7 on Days 1–5. The results of these tests are presented in Table 7 in terms of %T/C values which are the ratios of mean survival times of treated to control animals, expressed as percentages.

TABLE 7

In Vivo Activity of CL-1957E Against P388 Leukemia in Mice

| CL-1957E Dose (µg/kg/Injection) | % T/C |
|---|---|
| 200 | Toxic |
| 100 | 153 |
| 50 | 139 |
| 25 | 130 |

EXAMPLE 9

The cytotoxicity of CL-1957E against L1210 mouse leukemia cells and against human colon adenocarcinoma (HCT 8) cells was measured in vitro. The $ID_{50}$ values appear in Table 8.

TABLE 8

| Compound | L1210 Mouse Leukemia Cells | $ID_{50}$ Human Colon Adenocarcinoma Cells |
|---|---|---|
| CL-1957E | 0.0034 µg/ml | 0.0010 µg/ml |

The compound of the present invention forms pharmaceutically acceptable salts with organic and inorganic bases. Examples of suitable inorganic bases are ammonium hydroxide, sodium hydroxide, potassium hydroxide, sodium carbonate, calcium hydroxide, sodium bicarbonate, and the like. Pharmaceutically acceptable salts are also formed with amine cations derived from organic nitrogenous bases strong enough to form cations.

The pharmaceutically acceptable salts of the acid are prepared, for example, by suspending the acid in water and adjusting the pH with the pharmaceutically acceptable base, or by reacting the compounds with one equivalent of the pharmaceutically acceptable base in a solvent and removing the solvent under reduced pressure.

The term, pharmaceutically acceptable metal cation contemplates the positively charged ions derived from such metals as sodium, potassium calcium, magnesium, aluminum, zinc, iron, and the like. The salts are prepared by contacting the free acid form of the compound with an equivalent amount of the desired base in the conventional manner. The free forms may be regenerated by treating the salt form with an acid. For example, dilute aqueous acid solutions may be utilized to regenerate the free acid form from a respective salt. Dilute aqueous hydrochloric acid is suitable for this purpose. The free acid form differs from its respective salt forms somewhat in certain physical properties, such as solubility in polar solvents, but the salts are otherwise equivalent to the respective free acid form for purposes of the invention.

The term pharmaceutically acceptable amine cation contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

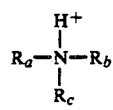

wherein $R_a$, $R_b$, and $R_c$, independently, are hydrogen, alkyl of from about one to about six carbon atoms, cycloalkyl of from about three to about six carbon atoms, aryl of about six carbon atoms, aralkyl of from about 7 to about 11 carbon atoms, hydroxyalkyl of from about two to about four carbon atoms, or monoarylhydroxyalkyl of from about 8 to about 15 carbon atoms, or, when taken together with the nitrogen atom to which they are attached, any two of $R_a$, $R_b$, and $R_c$ may form part of a 5- to 6-membered heterocyclic ring containing carbon, hydrogen, oxygen, or nitrogen, said heterocyclic rings and said aryl groups being unsubstituted or mono- or dialkyl substituted said alkyl containing from about one to about six carbon atoms. Illustrative therefore of $R_a$, $R_b$, and $R_c$ groups comprising pharmaceutically acceptable cations derived from ammonia or a basic amine are ammonium, mono- di- and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, pyridinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di-, and triethanolammonium, ethyldiethanolammonium, n-butylmonoethanolammonium, tris(hydroxymethyl)methylammonium, phenylmonoethanolammonium, and the like.

EXAMPLE 10

Preparation of the Potassium Salt of CL-1957E

Cooled potassium hydroxide solution (10 ml, 0.0176M) is added dropwise with stirring to a cooled solution of 100 mg (0.176 mmol) of CL-1957E in 2.5 ml of methanol. The resulting solution is concentrated in vacuo and then diluted with 40 ml of water. Two-milliliter aliquots of this solution are added to each of several 6-ml vials. Lyophilization of the contents of each vial affords a white solid corresponding, in each vial, to 5 mg of CL-1957E potassium salt.

EXAMPLE 11

Preparation of the Triethylammonium Salt of CL-1957E

A cooled solution of triethylamine (2.45 ml, 0.176 mmol) in 7.55 ml of water is added dropwise with stirring to a solution of 100 mg (0.176 mmol) of CL-1957E in 2.5 ml of methanol. The resulting solution is concentrated to a final volume of about 2 ml on a rotary evaporator and then diluted to 40 ml with water. Two-milliliter aliquots of this solution were added to each of several 6-ml vials. Lyophilization of the contents of each vial affords a white solid corresponding, in each vial, to 5 mg of CL-1957E triethylammonium salt, which was found to be soluble in water.

EXAMPLE 12

Preparation of the Sodium Salt of CL-1957E with Mannitol

Cooled sodium hydroxyde solution (10 ml, 0.0176M) is added dropwise to a cooled solution of 100 mg (0.176 mmol) of CL-1957E in 2.5 ml of methanol. The resulting solution is concentrated in vacuo to remove the methanol, and then 500 mg of mannitol contained in 10 ml of water is added to the concentrate. This mixture is diluted to 40 ml with water. Two-milliliter aliguots of this solution are added to each of several 6-ml vials. Lyophilization of the contents of each vial affords a white solid corresponding, in each vial, to 5 mg of CL-1957E sodium salt with mannitol as a bulking agent.

EXAMPLE 13

Preparation of the Sodium Salt of CL-1957E with Ascorbic Acid and Mannitol

Cooled sodium hydroxide solution (10 ml, 0.0176M) is added dropwise to a cooled solution of 100 mg (0.176 mmol) of CL-1957E in 2.5 ml of methanol. The resulting solution is concentrated in vacuo to remove the methanol, and then 500 mg of mannitol and 73.3 mg of ascorbic acid, both contained in 10 ml of water, are added to the concentrate. The resulting mixture is diluted to 40 ml with water. Two-milliliter aliquots of this solution are added to each of the several 6-ml vials. Lyophilization of the contents of each vial affords a white solid corresponding, in each vial, to 5 mg of CL-1957E sodium salt and 2.48 mg of ascorbic acid, with mannitol as a bulking agent.

The antibiotic compound CL-1957E, either in its free acid form, or in the form of one or more of its pharmaceutically acceptable salts, are useful for their antimicrobial or antitumor activity as pharmaceutical compositions in combination with a compatible pharmaceutically acceptable carrier. These compositions may also contain other antimicrobial and/or antitumor agents. The compositions may be made up in any pharmaceutically appropriate form for the desired route of administration. Examples of such forms include solid forms for oral administration as tablets, capsules, pills, powders and granules, liquid forms for topical or oral administration as solutions, suspensions, syrups, and elixirs, and forms suitable for parenteral administration such as sterile solutions, suspensions, or emulsions.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided active compound. In the table the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogenous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses as low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 5 to 100 mg according to the particular application and the potency of the active ingredient. The compositions can, if desired, also contain other compatible therapeutic agents.

In therapeutic use, the mammalian dosage range for a 70 kg subject is from 1 to 1500 mg/kg of body weight per day or preferably 2 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

We claim:

1. The compound CL-1957E having the name 19-(3,6-dihydro-3-methyl-6-oxo-2H-pyran-2-yl)-6-hydroxy-9-hydroxymethyl-3,5,7,11,15,17-hexamethyl-8-oxo-2,10,12,16,18-nonadecapentaenoic acid or a pharmaceutically acceptable salt thereof, said compound having the structure

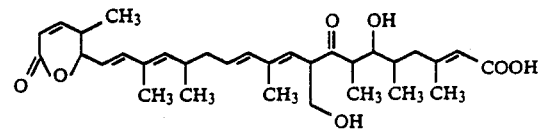

2. A compound in accordance with claim 1 being the sodium salt of 19-(3,6-dihydro-3-methyl-6-oxo-2H-pyran-2-yl)-6-hydroxy-9-hydroxymethyl-3,5,7,11,15,17-hexamethyl-8-oxo-2,10,12,16,18-nonadecapentaenoic acid.

3. A compound in accordance with claim 1 being the potassium salt of 19-(3,6-dihydro-3-methyl-6-oxo-2H-pyran-2-yl)-6-hydroxy-9-hydroxymethyl-3,5,7,11,15,17-hexamethyl-8-oxo-2,10,12,16,18-nonadecapentaenoic acid.

4. A compound in accordance with claim 1 being the calcium salt of 19-(3,6-dihydro-3-methyl-6-oxo-2H-pyran-2-yl)-6-hydroxy-9-hydroxymethyl-3,5,7,11,15,17-hexamethyl-8-oxo-2,10,12,16,18-nonadecapentaenoic acid.

5. A compound in accordance with claim 1 being the triethylammonium salt of 19-(3,6-dihydro-3-methyl-6-oxo-2H-pyran-2-yl)-6-hydroxy-9-hydroxymethyl-3,5,7,11,15,17-hexamethyl-8-oxo-2,10,12,16,18-nonadecapentaenoic acid.

6. A pharmaceutical composition for treating microbial infections comprising an antimicrobially effective amount of compound CL-1957E, said compound characterized as in claim 1, or a pharmaceutically acceptable salt thereof, together with a pharmaceutically acceptable carrier.

7. A pharmaceutical composition in accordance with claim 6 comprising a solution of the compound Cl-1957E and absolute ethanol.

8. A pharmaceutical composition in accordance with claim 6 comprising a solution of the compound CL-1957E and 95% ethanol.

9. A pharmaceutical composition in accordance with claim 6 comprising a solution of the compound CL-1957E and propylene glycol.

10. A pharmaceutical composition in accordance with claim 6 further containing ascorbic acid.

* * * * *